US006789942B2

(12) United States Patent  
Pillai et al.

(10) Patent No.: US 6,789,942 B2
(45) Date of Patent: Sep. 14, 2004

(54) C-ARM X-RAY APPARATUS WITH MECHANICALLY ADJUSTABLE BRAKE

(75) Inventors: Vipin J. Pillai, Bangalore (IN); Bindu Phillip, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/242,001

(22) Filed: Sep. 12, 2002

(65) Prior Publication Data

US 2004/0052335 A1 Mar. 18, 2004

(51) Int. Cl.$^7$ ................................. H05G 1/02
(52) U.S. Cl. .................... 378/197; 378/195; 378/198
(58) Field of Search ................. 378/195–198

(56) References Cited

U.S. PATENT DOCUMENTS

| 6,113,265 A | 9/2000 | Babler |
| 6,609,826 B1 * | 8/2003 | Fujii et al. ............... 379/198 |

FOREIGN PATENT DOCUMENTS

| CA | 2311307 | 6/1999 |
| DE | 1074211 B | 1/1960 |
| DE | 8812768 U | 12/1988 |
| JP | 10033516 A | 2/1998 |
| JP | 2001 525202 T | 12/2001 |
| WO | WO 9929144 A | 6/1999 |

* cited by examiner

Primary Examiner—Craig E. Church
(74) Attorney, Agent, or Firm—Joseph S. Heino; Carl B. Horton; Patrick M. Bergin

(57) ABSTRACT

A mechanically adjustable brake for use with a C-arm x-ray apparatus is generally comprised of a brake handle and an eccentric shaft support which, when rotated using the handle, actuates a cam and presses a brake pad into the C-arm. Movement of the C-arm is thus restricted when the brake is applied. The brake mechanism specifically includes a brake handle, a brake shaft, a cam mounted on the brake shaft, a plunger having a first end engaged with the cam and a second end having a brake. The brake handle is used to rotate the brake shaft and the cam, the cam pushes down on the plunger and the brake engages the C-arm. The brake mechanism further comprises a plunger support, a spring that is compressed when the brake is actuated and is decompressed when the brake is released thus permitting movement of the C-arm. The brake shaft is connected to the brake handle using an eccentric shaft support. The shaft support has an inner aperture having a center offset from the center of the outer perimeter and a plurality of parallel grooves in the outer perimeter of the shaft support that permit removal and advancement of the eccentric shaft support.

18 Claims, 7 Drawing Sheets

C-ARM X-RAY APPARATUS WITH MECHANICALLY ADJUSTABLE BRAKE

BACKGROUND OF THE INVENTION

1. Field of the Invention

The present invention relates generally to the area of x-ray imaging systems and devices used with such diagnostic x-ray systems. More specifically, the present invention relates to the field of a C-arm imaging apparatus incorporating a new and improved orbital braking mechanism for holding the C-arm in position relative to the yoke by use of a single piece yoke and for achieving wear compensation of the orbital brake without disassembly of the C-arm.

2. Background of the Invention

It is frequently desired to conduct an x-ray examination of a patient by positioning the x-ray equipment such that a number of different views of the area of interest, and from several different positions, may be obtained. It is also preferable to do so without the need to reposition the patient. Mobile C-arm x-ray diagnostic equipment, such as that shown in FIG. 1, has been developed to meet these needs and is now well known in the medical and surgical arts. The C-arm x-ray machine is especially useful in that it is small enough and mobile enough to be present in an operating or exam situation without requiring the physician to repeatedly move or requiring the patient to change positions to obtain a suitable image. This usage, however, also requires frequent movement and repositioning of the equipment itself.

C-arm imaging systems are widely used in the medical arts. Examples of their uses include bone density measurement and fluoroscopic imaging during surgical procedures. The term "C-arm" refers to the generally C-shaped member that has an x-ray source and an image receptor, or detector, mounted on opposing ends of the C-arm. In this fashion, x-rays emitted by the source are incident on and detected by the detector. The x-ray source and the detector are positioned such that when, for example, a human extremity is interposed between the x-ray source and the image receptor, thereby exposing the extremity to x-ray radiation, the receptor produces data representative of characteristics of the interposed extremity. The data produced is then displayed on a monitor and electronically saved.

The C-arm portion of the machine is normally mounted such that it is permitted two degrees of freedom. First, the C-arm track is slidably mounted to the C-arm support, or yoke, so as to be movable in relation to the yoke. This permits the x-ray source and image receptor to be moved rotatably about the arc of curvature of the track in the C-arm. Second, the C-arm support member permits rotation of the C-arm about its axis. Mobile C-arm machines also have a third degree of freedom in that they are free to move horizontally along the floor and a fourth in that the C-arm can be raised and lowered.

C-arm x-ray equipment must be delicately positioned in order to render the image or images desired or required by the physician. Unfortunately, the weight of the supporting structure makes it difficult to position the C-arm. Therefore, it is desirable to design a source of frictional drag between the C-arm and the C-arm's support member as well as on the C-arm track.

It is also desirable to balance the C-arm, the x-ray source, the x-ray detector and the Yoke so that relatively little physical effort is required to move the C-arm about the orbital rotation axis and the lateral rotation axis. One manner of accomplishing this is to design the C-arm such that its center of mass is as close as possible to the orbital and lateral rotation axes. Nearly balanced C-arms also require less braking force to be locked into place.

Prior devices are frequently equipped with a C-arm brake that can only be adjusted by opening the yoke. Some of these devices actually require a two-piece yoke. The device of the present invention eliminates the need for a two piece yoke and further eliminates the need for downtime while the yoke is being taken apart and the brake advanced.

BRIEF SUMMARY OF THE INVENTION

Accordingly, it is an object of the present invention to provide such a C-arm brake that allows for wear compensation while allowing for the use of a single piece yoke, which improves manufacturing simplicity and reduces cost. It is another object of the present invention is to allow adjustment of the brake without disassembly. Yet another object of the present invention is to provide a device that can accommodate for manufacturing variances. It is still another object of the present invention to provide such a device that requires relatively few parts and can be easily manufactured. It is yet another object of the present invention to provide an aesthetically pleasing and aseptic device overall.

The device of the present invention has obtained these objects. It provides for a yoke interposed between the support arm and the C-arm of the C-arm x-ray machine that provides support for the C-arm and also allows for a single piece yoke. The device of the present invention also provides a plurality of discrete adjustments of the brake with no disassembly of the yoke being required. The present invention further provides for a device that accommodates for small variances in manufacturing. The device of the present invention is also relatively simple to construct and easy to operate, in addition to being aesthetically pleasing. Additional objects and advantages of the device of the present invention will be set forth in the description that follows. Other objects and advantages may be learned by practice of the invention.

DETAILED DESCRIPTION OF THE INVENTION

The following detailed description is intended to describe the preferred embodiments that are depicted in the figures.

It is to be understood that changes could be made to that which is specifically described and shown that would still fall within the scope of the present invention.

Figure 1:
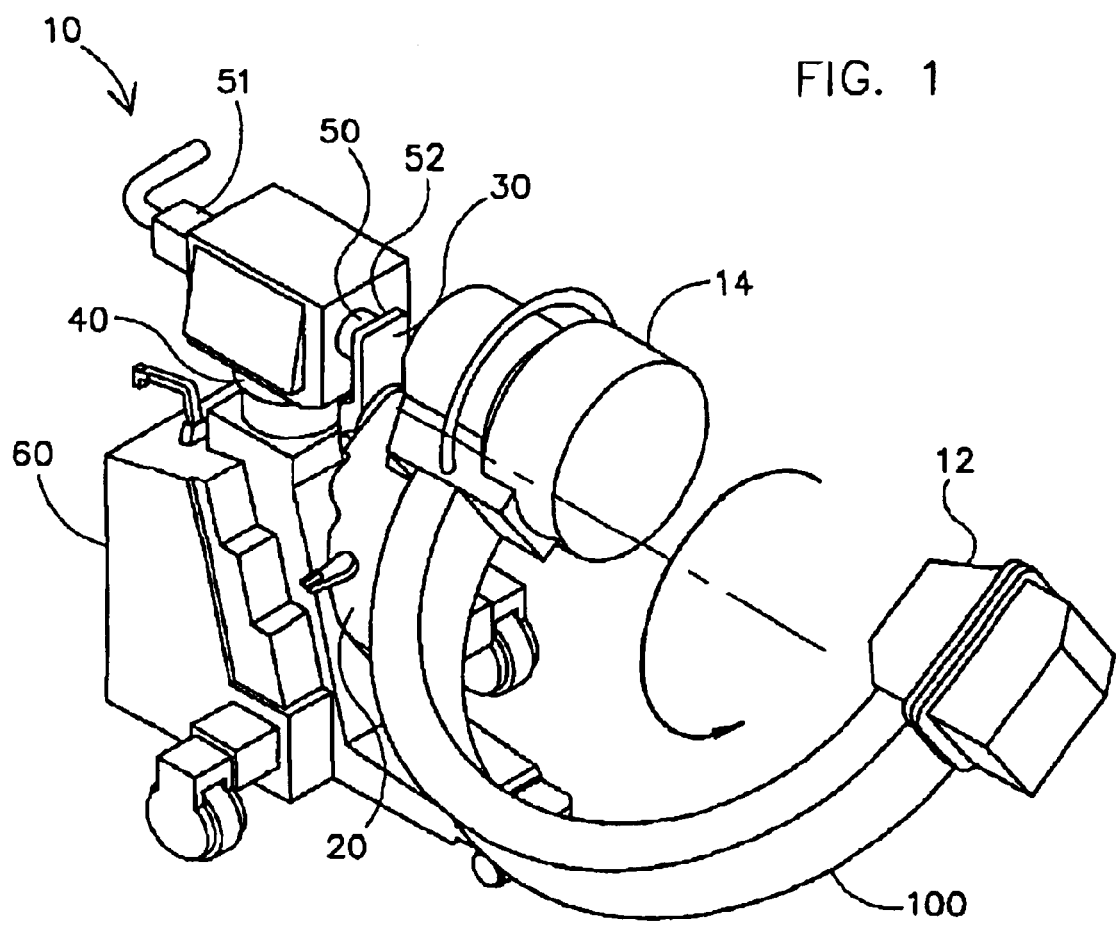
FIG. 1 is a top, front and right side perspective view of a C-arm x-ray machine constructed in accordance with the device of the present invention.

Referring now to the drawings in detail, wherein like numbered elements refer to like elements throughout, FIG. 1 depicts the basic components of the imaging system such as that used in the present invention. In general, a C-arm x-ray imaging machine, generally identified 10, is comprised of the following components: an x-ray source 12, an image receptor 14, an image processing system, a display and viewing system, a high voltage generator and a control unit. Disposed between the x-ray source 12 and the receptor 14 is the patient (not shown) or other object of the radiographic study.

The x-ray source 12 preferably comprises an x-ray tube and a high-voltage generator. The high-voltage generator is connected to an adjustable high-voltage power supply capable of generating approximately −70 kV to −120 kV.

When the x-ray system is being operated, the charged particle beam strikes the target and generates x-ray photons. The x-ray photons pass through a collimator and form an x-ray beam. The x-ray beam has an axis that is substantially aligned with the center of the active area of the x-ray detector. X-rays that have passed through the patient are detected and later processed for some form of interpretation. The detection and recording system is generally comprised of the image receptor 14. The image receptor 14 captures the x-ray photons scanned across the imaging object and converts them to electrical signals. The impulses are then converted to digital data and either stored or fed immediately into a computer for image reconstruction. The imaging process system generally consists of a computer with a software package that reconstructs the image and displays the image on a screen and a device that provides for storage of the image.

The display system and the control unit are normally remotely operated. Thus the operator can be shielded from radiation but still perform the x-ray study. Alternatively, the entire system can be placed in an examining or operating room so that the health care provider can view images of the patient in real time.

The mobile C-arm x-ray imaging machine, generally identified 10, includes a wheeled support base 60. In a preferred embodiment, the support base 60 is a generally rectangular upright body that may be equipped with one or more video monitors and has an upper portion or vertically extendable column 40 with an extendable cross arm 50. The extendable cross arm 50 has a first portion 51 slidably mounted within the vertically extendable column 40 and a second end 52 having an aperture 53 defined in the cross arm 50. The support base 60 is important to the imaging machine 10 in that it provides a platform for the yoke 20 and the C-arm 100. Therefore, the support base 60 should have a footprint large enough such that the yoke 20 and C-arm 100 are permitted to rotate without the danger of tipping the x-ray machine 10.

The device of the present invention, unlike previous devices, provides a support arm 30 between the yoke 20 and the support base 60. The support arm 30 is designed to lower the axis of rotation such that the axis of rotation coincides, or very nearly coincides, with the center of gravity of the C-arm 100. The closer the center of gravity of the C-arm 100 to the axis of rotation of the C-arm 100, the smaller the force required to rotate the C-arm 100.

The yoke 20, as shown in FIG. 1, has a first end 21 attached to the support arm 30 and a second end 22 attached to the C-arm 100. Since the C-arm 100 is an overhanging part, strength of the yoke 20 and the safety of patients and healthcare workers is a consideration. Therefore, a relatively high safety factor is used. The requirement for a high factor of safety in addition to the requirement that the yoke 20 be lightweight led designers to choose an aluminum alloy for fabrication of that part.

Obviously, some manner of immobilizing the C-arm 100 with respect to the yoke 20 is required for accurate imaging. The device of the present invention provides for a mechanically adjustable brake 200 that accommodates for both wear on the brake and production inconsistencies. The brake mechanism 200 is generally comprised of a brake handle 210, an eccentric shaft support 220, a cam 230, a plunger 240, a plunger support mechanism 250, a spring 260, and a brake pad 270.

Figure 2:
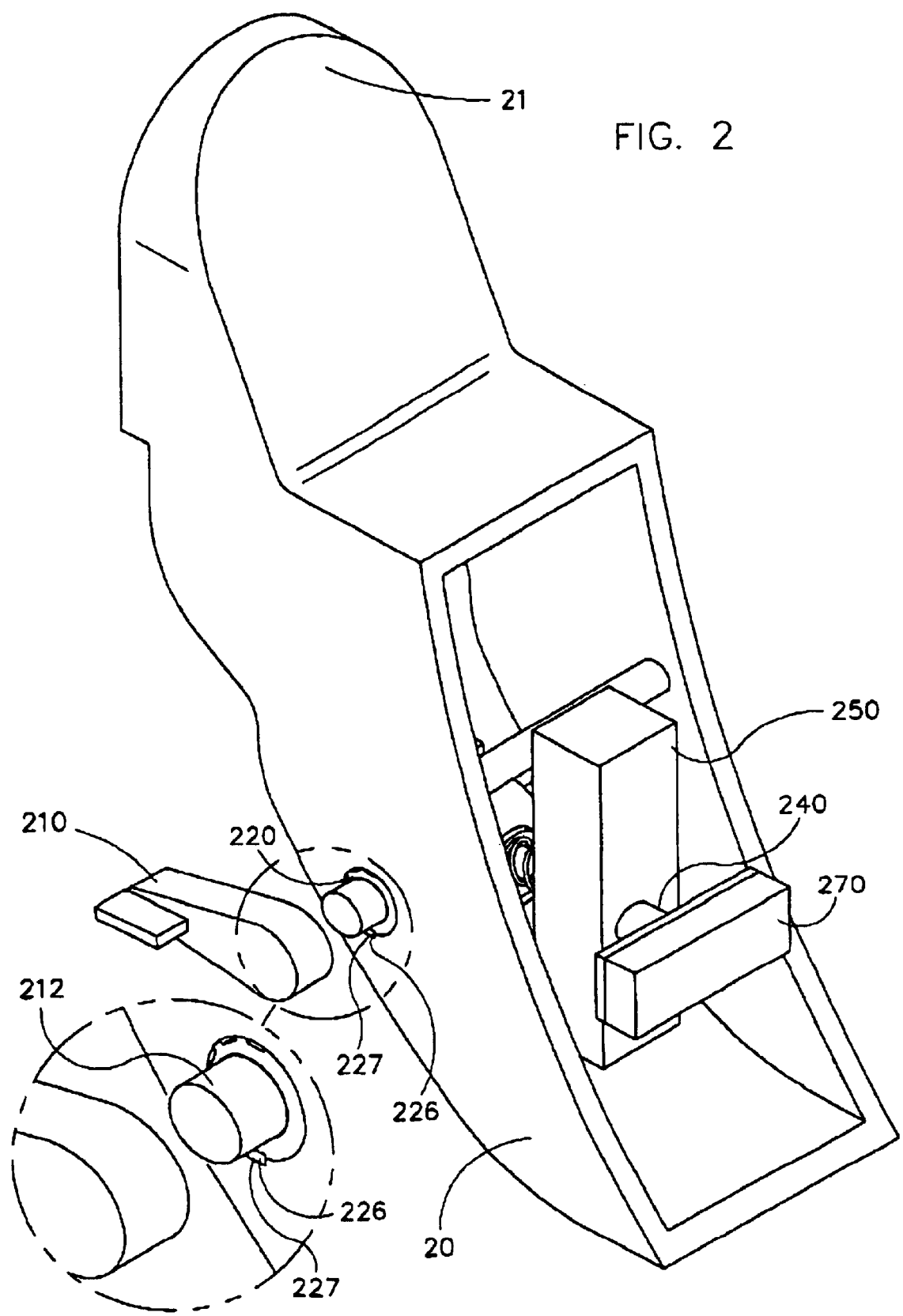
FIG. 2 is a top, front and left side perspective view of the yoke and brake mechanism constructed in accordance with the present invention and showing an enlarged view of the brake handle and eccentric shaft support.
Figure 3:
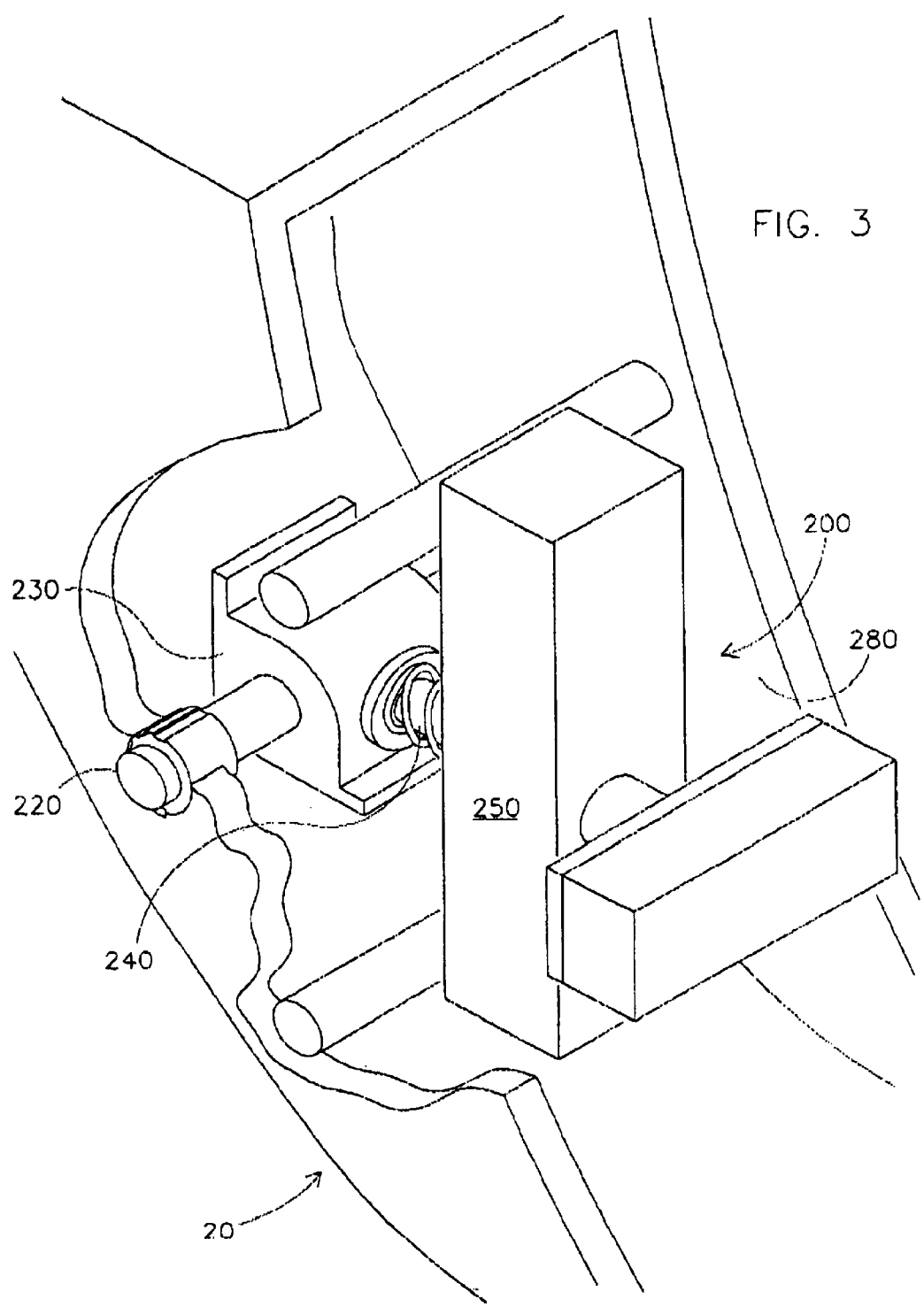
FIG. 3 is a further enlarged top, front and left side and partially cut-away perspective view of the yoke and brake mechanism shown in FIG. 3A.
Figure 4A:
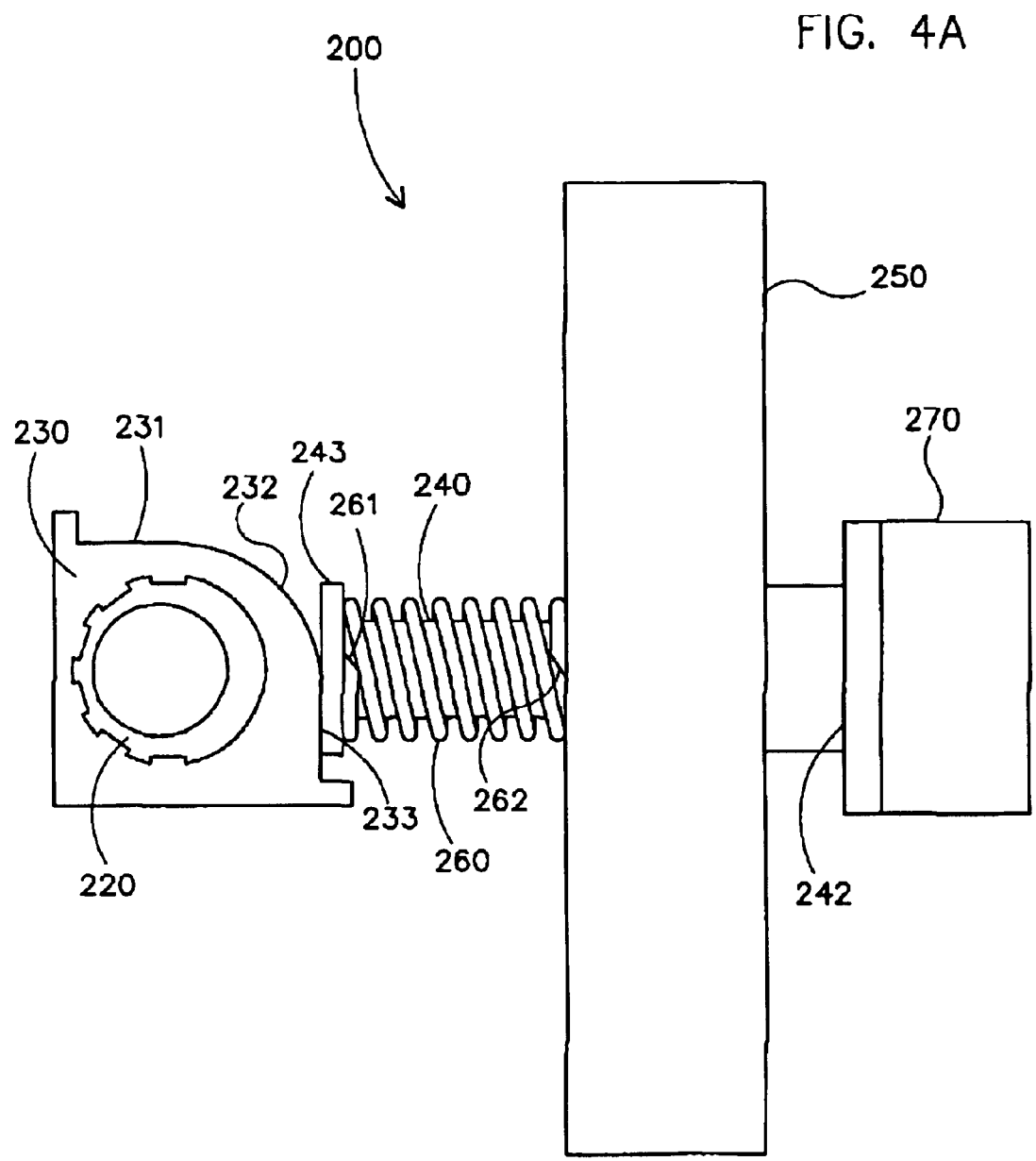
FIG. 4A is a further enlarged left side elevational view of the brake mechanism wherein the eccentric shaft support is shown being used at its lowest setting.
Figure 4B:
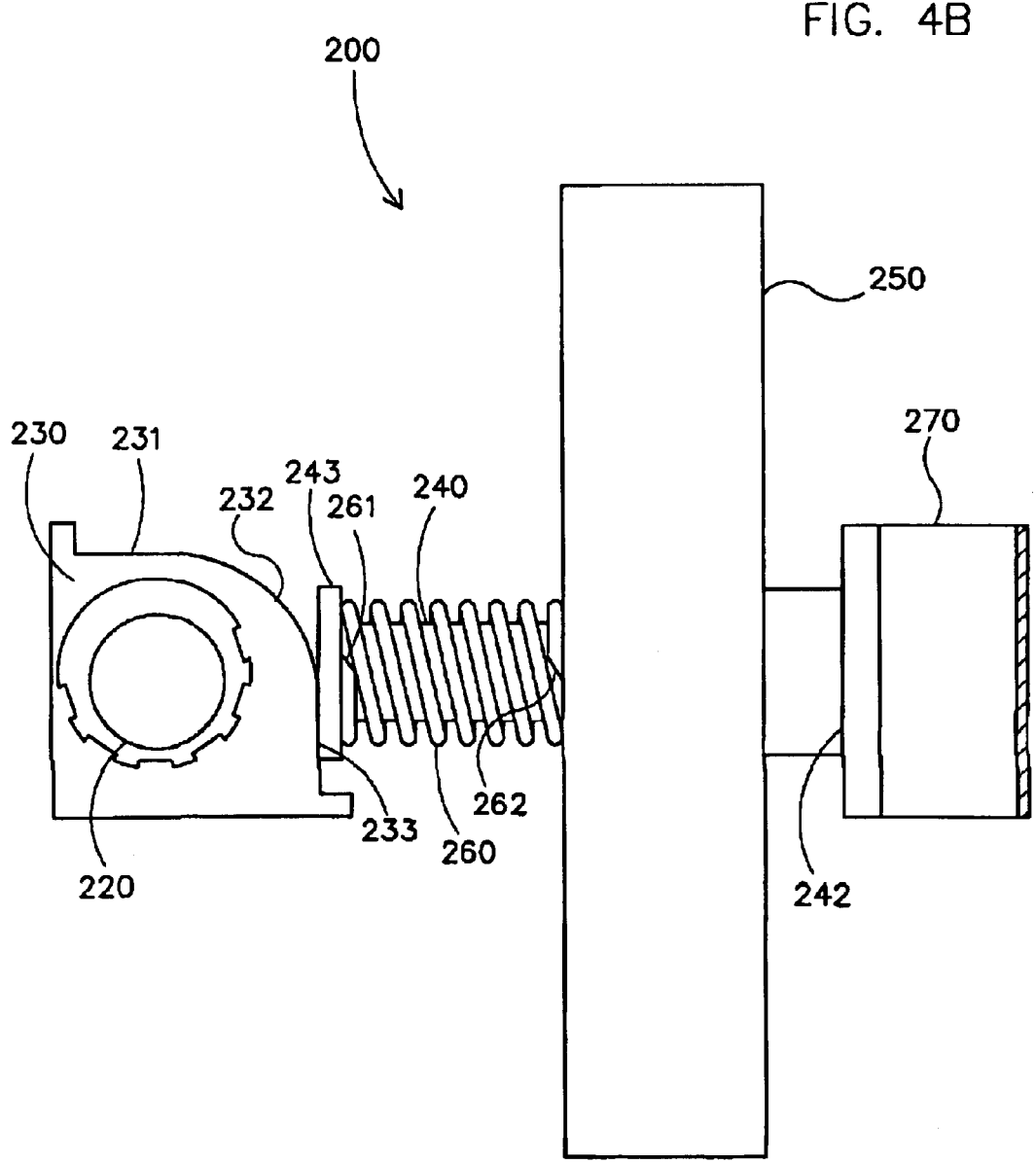
FIG. 4B is another left side elevational view of the brake mechanism illustrated in FIG. 4A and showing one of the midrange settings of the eccentric shaft support.
Figure 4C:
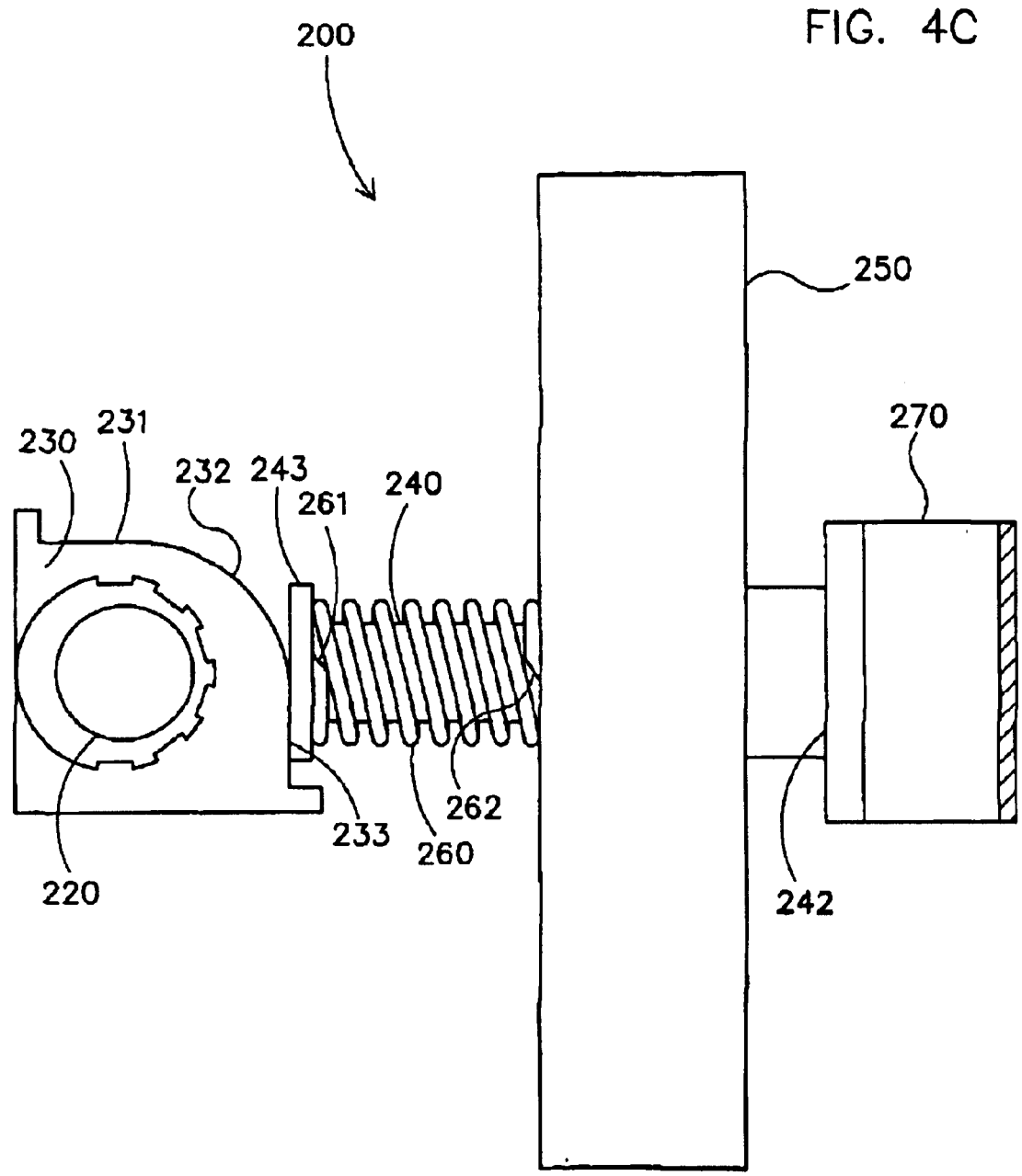
FIG. 4C is still another left side elevational view of the brake mechanism illustrated in FIGS. 4A and 4B wherein the most extreme, or deepest, plunger settings of the eccentric shaft support is shown.
Figure 5:
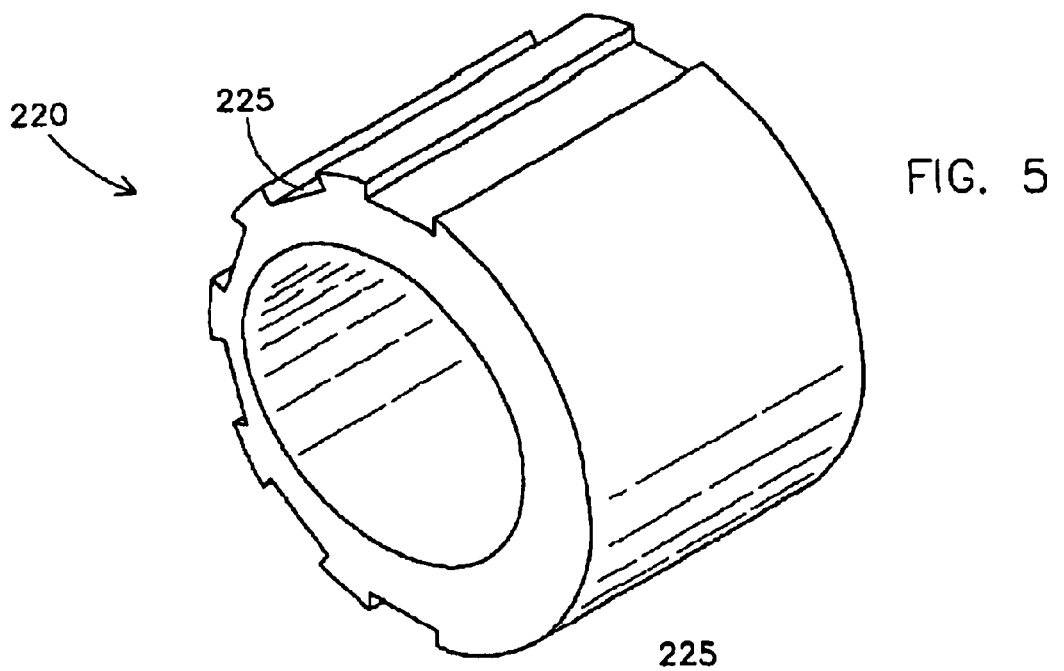
FIG. 5 is a top, front and left side perspective view of an eccentric shaft support constructed in accordance with the present invention.
Figure 6:
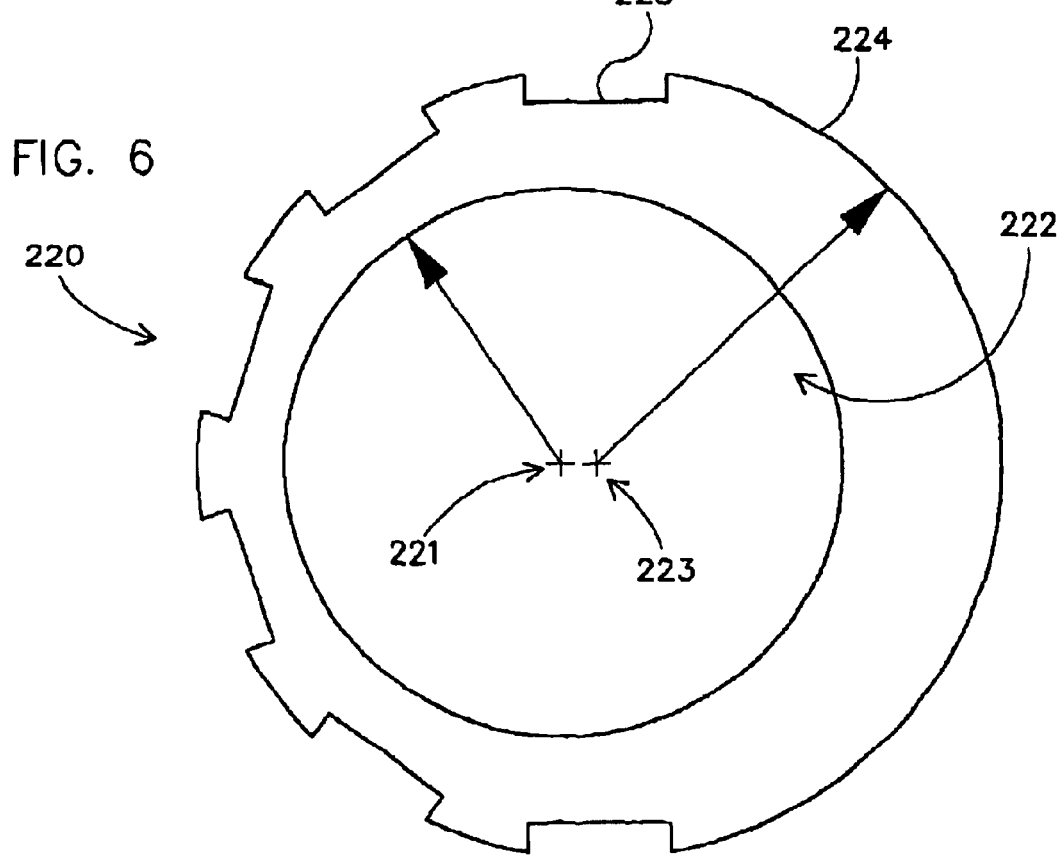
FIG. 6 is a left side elevational view of the shaft support shown in FIG. 5.

The exterior portion of the brake handle 210 can take nearly any form the designer desires or requires. The brake handle 210 includes a brake handle rod 212 that is insertable into the eccentric shaft support 220. As shown in FIG. 2, it will be seen that the eccentric shaft support 220 employs an eccentric mounting technique with discrete steps to advance the cam and urge the brake pad 270 forwardly. In the preferred embodiment, this eccentricity is accomplished by design in that the center 221 of the inner shaft 222 is offset about 0.75 millimeters from center 223 of the outer perimeter 224 of the eccentric shaft support 220. See FIG. 6. The inventors are also aware a range of offset is acceptable, and do not intend to limit themselves to 0.75 mm offset. The outer perimeter 224 of the bush 220 features a plurality of longitudinally extending and parallel grooves 225, each groove permitting additional forward advancement of the brake 270. It is also to be understood that the opposite end of the brake handle rod 212 is engageable with a second bush eccentric shaft support 220 of similar configuration and a second brake handle 210. In this fashion, each brake handle 210 to either side of the yoke 20 is used to rotate the eccentric shaft support 220. The shaft support 220 of like configuration may be used for each position because of the way that the grooves 225 are defined within the shaft support 220 which allows for rotation in each direction when a pair of such supports 220 are placed such that one is opposite the other.

In application, the eccentric shaft support 220 rotates the cam 230. The cam 230 itself is an eccentric shape, with a first edge 231 providing the plunger 240 enough clearance such that the brake 270 is off the C-arm 100 and the C-arm 100 is permitted to rotate. The cam 230 has a corner 232 that, when rotated, pushes the brake 270 downwardly and a second edge 233 that is designed to press the brake pad 270 into the C-arm 100 such that the C-arm 100 is not permitted to move until the coefficient of friction is overcome.

The cam 230 pushes the plunger 240 downwardly. The plunger 240 has a first end 241 with a lip 243 and a second end connected to the brake pad 270. The plunger then pushes the brake pad 270 downwardly when the cam 230 is rotated.

It is also desired in the medical field to provide a device that can be easily moved as well as securely locked into place. The device of the present invention provides a spring 260 for retraction of the plunger 240 with respect to the cam 230.

The plunger support 250 is attached to the inside walls of the yoke 20. In this role, the plunger support 250 provides a platform for the spring 260. The first end 261 of the spring 260 rests on the lip of the plunger 243 and the second end 262 of the spring 260 rests on the plunger support 250. Therefore, as the cam 230 is rotated to relieve the pressure on the C-arm 100, the spring 260 will operate to lift the brake pad 270 off of the C-arm 100.

The brake pad 270 is attached to the second end 242 of the plunger 240. The brake pad 270 is of a general design those familiar in the art of brakes will recognize. In any event, the brake pad 270 should be fabricated from a material that produces an acceptable amount of friction with respect to the C-arm 100.

To adjust the advancement of the plunger 240, one simply removes the eccentric shaft support 220 from the yoke 20 using a keyway, or groove 225 in the yoke 20 around the eccentric shaft support 220 and advances the eccentric shaft support 220 from each side of the yoke 20 by one of the discrete settings. The key 226 is then reinserted into the yoke keyway 227 and groove 225 to hold the eccentric shaft support 220 in its new position. It is also important to note that at no time is the patient able to access the shaft. It is hidden from the patient by the handle 270. If the handle does not cover the entire opening, a sticker providing directions is employed to cover the eccentric shaft 220.

It is to be understood that the invention is not limited to the embodiments set forth herein but that the invention may be carried out in other ways without departure from the spirit of this invention. Based on the foregoing, it will be apparent that there has been provided a C-arm brake that allows for wear compensation while allowing for the use of a single piece yoke, which improves manufacturing simplicity and reduces cost; that allows adjustment of the brake without disassembly and can accommodate for manufacturing variances; that requires relatively few parts and provides an aesthetically pleasing and aseptic device overall.

| Parts List: | |
| --- | --- |
| 10 | C-arm x-ray imaging machine |
| 12 | x-ray source |
| 14 | image receptor |
| 20 | yoke |
| 30 | support arm |
| 37 | brake mechanism in support arm |
| 38 | support arm brake handle |
| 40 | vertical colunm |
| 50 | cross arm |
| 51 | first end of the cross arm |
| 52 | second end of the cross arm |
| 53 | aperture in cross arm |
| 60 | support base |
| 100 | C-arm |
| 200 | mechanically adjustable brake |
| 210 | brake handle |
| 212 | brake handle rod |
| 220 | eccentric shaft support |
| 221 | center of the inner eccentric shaft |
| 222 | inner shaft |
| 223 | center of the outer shaft |
| 224 | outer perimeter of shaft |
| 225 | parallel groove in shaft |
| 230 | cam |
| 231 | first edge of the cam |
| 232 | corner of the cam |
| 233 | second edge of the cam |
| 240 | plunger |
| 241 | first end of the plunger |
| 242 | second end of the plunger |
| 243 | lip on the first end of the plunger |
| 250 | plunger support |
| 260 | spring |
| 261 | first end of the spring |
| 262 | second end of the spring |
| 270 | brake pad |

What is claimed is:

1. A C-arm x-ray apparatus comprising
a mobile support base,
a vertically extendable column,
an extendable cross arm having a first end slidably attached to the vertically extendable column and a second end,
a support arm having a first end attached to the second end of the cross arm and a second end,
a yoke having a first end attached to the second end of the support arm and a second end,
a C-arm attached to the second end of the yoke,
a brake handle,
a brake operated by the brake handle, said brake handle being exterior to the yoke and said yoke having a hollow interior portion,
a brake shaft wherein the shaft support is connected to the brake handle using an eccentric shaft support,
a cam mounted on the brake shaft,
a plunger engaged with the cam,
a brake pad at the end of said plunger,
a plunger support mounted within the yoke and having an apertur permitting the plunger to pass,
a spring situated between the cam and the plunger support,
wherein, when the brake handle is operated, the brake handle turns the brake shaft which rotates the cam, and the cam then pushes the plunger, compresses the spring and sets the brake pad onto the C-arm,
an x-ray source,
an image receptor,
wherein the image receptor and the x-ray source are mounted on opposing ends of the C-arm.

2. The apparatus of claim 1 wherein the spring encircles the plunger.

3. The apparatus of claim 2 wherein the eccentric shaft support has an inner aperture having a center offset from the center of the outer perimeter and a plurality of parallel grooves in the outer perimeter of the shaft support that permit removal and advancement of the eccentric shaft support.

4. The apparatus of claim 3 wherein the center of the inner perimeter of the eccentric shaft is offset 0.75 mm from the center of the outer perimeter of the eccentric shaft support.

5. A C-arm x-ray apparatus comprising
a mobile support base,
a vertically extendable column,
an extendible cross arm having a first end slidably attached to the vertically extendible column and a second end,
a support arm having a first end attached to the second end of the cross arm and a second end,
a yoke having a first end attached to the second end of the support arm and a second end,
a C-arm attached to the second end of the yoke,
a brake handle,
a brake shaft wherein the brake shaft is connected to the brake handle using an eccentric shaft support,
a cam mounted on the brake shaft,
a plunger having a first end engaged with the cam and a second end having a brake,
wherein the brake handle is used to rotate the brake shaft and the camsuch that the cam pushes down on the plunger and the brake engages the C-arm,
an x-ray source,
an image receptor,
wh rein the imag receptor and th x-ray source are mounted on opposing ends of the C-arm.

6. The apparatus of claim 5 wherein the brake mechanism further comprises a plunger support, a spring, said spring being compressed when the brake is actuated and decompressed when the brake is released thus permitting movement of the C-arm.

7. The apparatus of claim 6 wherein the eccentric shaft support has an inner aperture having a center offset from the center of the outer perimeter and a plurality of parallel grooves in the outer perimeter of the shaft support that permit removal and advancement of the eccentric shaft support.

8. The apparatus of claim 7 wherein the center of the inner perimeter of the eccentric shaft is offset 0.75 mm from the center of the outer perimeter of the eccentric shaft support.

9. A C-arm x-ray apparatus comprising a mobile support base, a vertically extendable column, an extendable cross arm having a first end slidably attached to the vertically extendable column and a second end, a support arm having a first end attached to the second end of the cross arm and a second end, a yoke having a first end attached to the second end of the support arm and a second end, a C-arm attached to the second end of the yoke, a brake mechanism alternately prohibiting and permitting motion comprising a brake handle, a brake shaft wherein said brake shaft is connected to the brake handle using an eccentric shaft support, a cam, a plunger having a first end engaged with the cam and a second end attached to a brake, an x-ray source, an image receptor, wherein the image receptor and the x-ray source are mounted on opposing ends, of the C-arm.

10. The apparatus of claim 9 wherein the brake mechanism further comprises a plunger support designed to fit between the walls of the yoke and offer torsional support for the yoke, a spring, said spring being compressed when the brake is actuated and decompressing when the brake is released thus permitting movement of the C-arm.

11. The apparatus of claim 10 wherein the eccentric shaft support has an inner aperture having a center offset from the center of the outer perimeter and a plurality of parallel grooves in the outer perimeter of the shaft support that permit removal and advancement of the eccentric shaft support.

12. The apparatus of claim 11 wherein the center of the inner perimeter of the eccentric shaft is offset 0.75 mm from the center of the outer perimeter of the eccentric shaft support.

13. A C-arm x-ray apparatus comprising a mobile support base, a vertically extendable column, an extendable cross arm having a first end slidably attached to the vertically extendable column and a second end, a support arm having a first end attached to the second end of the cross arm and a second end, a yoke having a first end attached to the second end of the support arm and a second end, a C-arm attached to the second end of the yoke, a brake mechanism alternately prohibiting and permitting motion comprising a brake handle, a brake shaft attached to the brake handle with an eccentric shaft support, a cam encircling the brake shaft, a plunger having a first end engaged with the cam and a second end attached to a brake, a plunger support designed to fit between the walls of the yoke and offer torsional support to the yoke, a spring, said spring being compressed when the brake is actuated and decompressing when the brake is release thus permitting movement of the C-arm, an x-ray source, an image receptor, wherein the image receptor and the x-ray source are mounted on opposing ends of the C-arm.

14. The apparatus of claim 13 wherein the eccentric shaft support has an inner aperture having a center offset from the center of the outer perimeter and a plurality of parallel grooves in the outer perimeter of the shaft support that permit removal and advancement of the eccentric shaft support.

15. The apparatus of claim 14 wherein the center of the inner perimeter of the eccentric shaft is offset 0.75 mm from the center of the outer perimeter of the eccentric shaft support.

16. A brake mechanism for alternately permitting and prohibiting movement of the C-arm of a C-arm x-ray imaging machine comprising a brake handle, a brake shaft connected to the brake handle with an eccentric shaft support, a cam mount d on said brake shaft, a plunger having a first end engaged with the cam and a second end attached to a brake, a plunger support having an aperture permitting passage of and movement of the plunger, said plunger being designed to fit between the walls of the yoke and offer torsional support to the yoke, a spring, said spring being compressed when the brake is actuated and decompressing when the brake is release thus permitting movement of the C-arm.

17. The apparatus of claim 16 wherein the eccentric shaft support has an inner aperture having a center offset from the center of the outer perimeter and a plurality of parallel grooves in the outer perimeter of the shaft support that permit removal and advancement of the eccentric shaft support.

18. The apparatus of claim 17 wherein the center of the inner perimeter of the eccentric shaft is offset 0.75 mm from the center of the outer perimeter of the eccentric shaft support.

* * * * *

UNITED STATES PATENT AND TRADEMARK OFFICE
CERTIFICATE OF CORRECTION

PATENT NO. : 6,789,942 B2  
APPLICATION NO. : 10/242001  
DATED : September 14, 2004  
INVENTOR(S) : Vilpin J. Pillai et al.

Page 1 of 1

It is certified that error appears in the above-identified patent and that said Letters Patent is hereby corrected as shown below:

Column 5, line 36, "colunm" should read -- column --.

Column 6, line 18, "apertur" should read -- aperture --.

Column 6, line 60, "camsuch" should read -- cam such --.

Column 6, line 64, "wh rein" should read -- wherein --.

Column 6, line 64, "imag" should read -- image --.

Column 6, line 64, "th" should read -- the --.

Signed and Sealed this

Eighth Day of January, 2008

JON W. DUDAS  
*Director of the United States Patent and Trademark Office*